United States Patent [19]

Jagadeeswaran

[11] Patent Number: 5,395,521
[45] Date of Patent: Mar. 7, 1995

[54] AUTOMATED COLUMN EQUILIBRATION, COLUMN LOADING, COLUMN WASHING AND COLUMN ELUTION

[75] Inventor: Pudur Jagadeeswaran, San Antonio, Tex.

[73] Assignee: Board of Regents, The University of Texas System, Austin, Tex.

[21] Appl. No.: 707,880

[22] Filed: May 31, 1991

[51] Int. Cl.$^6$ ............................................. B01D 15/08
[52] U.S. Cl. ................................ 210/198.2; 210/143; 210/656; 96/103
[58] Field of Search ............ 210/635, 656, 659, 198.2, 210/143; 55/67, 386; 422/70; 436/161, 162; 96/101, 102, 103; 95/82

[56] References Cited

U.S. PATENT DOCUMENTS

| 3,478,886 | 11/1969 | Hornbeck | 210/198.2 |
| 3,583,230 | 6/1971 | Patterson | 210/198.2 |
| 3,623,381 | 11/1971 | Crepin | 210/198.2 |
| 3,692,669 | 9/1972 | Bauman | 210/198.2 |
| 3,902,849 | 9/1975 | Barak | 210/198.2 |
| 3,925,207 | 12/1975 | Scriba | 210/198.2 |
| 3,954,617 | 5/1976 | Ishimatsu | 210/198.2 |
| 3,963,614 | 6/1976 | Ozawa | 210/198.2 |
| 4,214,993 | 7/1980 | Forsythe | 210/198.2 |
| 4,257,884 | 3/1981 | Lim | 210/656 |
| 4,652,529 | 3/1987 | Collins | 210/656 |
| 4,654,311 | 3/1987 | Khanna | 210/656 |
| 4,680,120 | 7/1987 | Ramsden | 210/656 |
| 4,753,775 | 6/1988 | Ebersole et al. | 422/81 |
| 4,766,082 | 8/1988 | D'Autey | 210/198.2 |
| 4,892,654 | 1/1990 | Nickerson | 210/198.2 |
| 4,900,446 | 2/1990 | Anderson | 210/198.2 |
| 5,021,162 | 6/1991 | Sakamoto | 210/198.2 |
| 5,045,208 | 9/1991 | Sanford | 210/198.2 |
| 5,091,092 | 2/1992 | Newhouse | 210/198.2 |
| 5,100,557 | 3/1992 | Nogami | 210/198.2 |
| 5,107,908 | 4/1992 | Newhouse | 210/198.2 |

FOREIGN PATENT DOCUMENTS

| 0393185 | 10/1990 | European Pat. Off. | 210/198.2 |
| 625691 | 7/1989 | France | 210/198.2 |
| 8900305 | 7/1989 | France | 210/198.2 |
| 3717211C | 12/1988 | Germany | 210/198.2 |

OTHER PUBLICATIONS

Hassan, Mithal et al., "Utilization of a computer-controlled laboratory workstation (Biomek 1000) in routine radioimmunoassay laboratory," Computers in Biology and Medicine, vol. 20, No. 3, Pergamon Press, GB, pp. 185–191 Sep. 1990.

Castellani, William J. et al., "Robotic Sample preparation evaluated for the immunochemical determination of cardiac isoenzymes," Clinical Chemistry, vol. 32, No. 9, Sep. 1986 pp. 1672–1676.

Prusiner et al., "Vacuum manifold for rapid assay of enzymes using radioactive tracers and ion exchange chromatography," Review of Scientific Instruments, vol. 42, No. 4, Apr. 1971, New York pp. 493–494.

Excerpt from Beckman brochure entitled "Biomek TM Supplies," pp. 11-1 to 11-2 (undated).

Beckman brochure entitled "Biomek® 1000 Automatic Laboratory Work Station" (11 pages) (undated).

Bethesda Research Laboratories Life Technologies, Inc. brochure entitled "NACS PREPAK® Instruction Manual" (42 pages) (undated).

PCT application WO 88/09201 entitled "Process and Device for Separating and Cleaning Molecules" to Werner Dec. 1988 (entire document).

Jagadeeswaran, "Biofeedback," *Bio Techniques*, vol. 12, 3:336–339 (1992).

Primary Examiner—Ernest G. Therkorn
Attorney, Agent, or Firm—Arnold, White & Durkee

[57] ABSTRACT

Method and apparatus for automatic chromatographic column operations, including column equilibration, column loading, column washing, and column elution. A novel pipette tip column is shown which is packed with a binding material sandwiched between two permeable spheres.

22 Claims, 1 Drawing Sheet

AUTOMATED COLUMN EQUILIBRATION, COLUMN LOADING, COLUMN WASHING AND COLUMN ELUTION

BACKGROUND OF THE INVENTION (1) Field of the Invention

This invention relates generally to automated chromatographic column operations, including column equilibration, column loading, column washing, and column elution. More particularly, the invention resides in a system in which a chromatographic column is moved in an automatic programmed sequence from one fluid source or discharge point to another. The invention is especially directed at the adaptation of an automatic pipetting system to an automatic chromatographic system.

(2) Description of the Prior Art

Many laboratory procedures rely upon column chromatographic methods. These procedures include the purification of DNA and oligonucleotides, preparation of poly A RNA and high molecular weight genomic DNA, and the recently developed column-based solid phase method of performing Maxam-Gilbert sequencing reactions. See "Use of Reverse-Phase Chromatography in the Maxam-Gilbert Method of DNA Sequencing: A Step Toward Automation," Jagadeeswaran, P. and Kaul, R. K., *Gene Analysis Techniques*, 3:79–85 (1986). In a multi-step procedure such as Maxam-Gilbert sequencing reactions, using commercially available columns and running them is a labor intensive process.

Robotic pipetting machines are well known in the art. For instance, the Biomek® 1000 Automated Laboratory Workstation (Beckman; 2500 Harbor Boulevard, Fullerton, Calif.) comprises a robotic arm which can hold a pipette tool and is capable of vertical and horizontal (forward and backward) movement. The Biomek® 1000 includes a platform which carries pipette tools, and separate storage ports which are holding places for pipette tips and fluids. The Biomek® 1000 can be programmed to move a pipette tool and connect to a pipette tip in such a manner as to enable the tool to intake and discharge liquid through the pipette tip. Typically, the Biomek® 1000 is programmed to move a pipette tool to a pipette storage location, connect the tool to a pipette tip, move to an instructed port which holds a liquid, pick up an instructed amount of liquid, and deliver this liquid to another location.

SUMMARY OF THE INVENTION

A general object of this invention is to provide an improved chromatographic system capable of automatic column equilibration, column loading, column washing, and column elution. In one embodiment of this invention an automatic pipetting apparatus is adapted to provide such a chromatographic system. The pipette tips used in the automatic pipetting apparatus are modified to perform as chromatographic columns, and to be transferred by the automatic pipetting machine from one position to another.

In a general aspect, the present invention comprises a vertically disposed column capable of holding a charge of a binding material or chromatographic medium; a plurality of column stations including a storage position, at least one separate fluid dispensing station, at least one separate receptacle station; and an automatic column handler programmable to automatically engage the column, move the column sequentially between a plurality of said stations, receive fluids at the dispensing stations, and discharge fluids at the receptacle stations. In a preferred form, the binding material holders employed with the invention are miniature columns which are necked or otherwise configured to receive a first permeable plug above a charge of chromatographic medium binding material within the column, and a second permeable plug below the charge. The plugs are configured to retain a charge of chromatographic medium between them, and to enable fluids to permeate through the plugs. At least one of the plugs is removable from the column, so as to enable the column to be charged with a chromatographic medium. Preferred plugs are unitary elastomeric members which are capable of being received and held by recesses, grooves, necked sections, or other internal structural seat-like features of the column. Thus, it is especially preferred that a plug be readily forced to seat within such a structural feature, and also be readily recovered. When seated within a column, it is desired that the plug seal against the internal wall of the column such that fluid will permeate through the body of the plug in preference to its periphery.

It is also preferred that the column for the chromatographic medium be a pipette-like member having a relatively long diameter central section and an extended necked section of smaller diameter. Indeed, an especially preferred column is a member resembling a pipette tip such as are employed with conventional automatic pipetting machines such as the Biomek® 1000. These machines are equipped and programmed to move pipette tips from one station to another, where the automatic pipetting machine then typically aspirates or discharges fluids through the pipette tips. In adapting the present invention to such apparatus, a pipette-shaped column is charged with a chromatographic medium binding material, and is moved from one station to another. The fluid dispensing and receptacle stations may be prepared by modifying existing fluid reservoir ports on the Biomek® 1000.

The Biomek® 1000 pipette tips are more preferably modified in accordance with the invention to become miniature chromatographic columns by preferably placing a porous permeable polyethylene sphere into the large end of the pipette tip and then pushing the sphere into location just above the "neck" of the pipette tip. The sphere is conveniently pushed into location with a steel rod. The sphere is then topped with a specific amount of a selected resin, chromatographic medium, or other binding material. A second porous permeable polyethylene sphere is then placed on top of the medium and firmly packed with the steel rod. The spheres prevent the binding material from moving during fluid intake and discharge operations performed by an automatic pipetting machine. Once correctly packed, these pipette tips became miniature chromatographic columns and are herein referred to as "columns."

Once a pipette tip is improved as described above, it is possible to program an automated pipetting apparatus to connect to a column, and then automatically equilibrate, load, wash, and elute the column. This procedure is performed by preparing an automatic pipetting apparatus with a packed column, a charging fluid source, an elution fluid source, a charging fluid discard location, and an elution fluid storage location. The packed column may be one of a plurality of such columns stored systematically in a suitable column storage facility. As used in this specification, "charging fluid" means any fluid used to equilibrate, load, or wash the column. In some instances the charging fluid may also include a fluid used to elute the column, although preferably the eluting step takes place after the charging step. "Fluid" means any gas or liquid.

Once prepared, the apparatus is programmed and operated to perform the following steps: move a pipette handling tool to the packed column storage; connect to a packed column so as to allow intake and discharge of fluid through the column; move to the charging fluid source; charge the column by intaking charging fluid into the column; move the column to the charging fluid discard location; and discharge the charging fluid. Successive selected fluids may be drawn into the column and discharged to successively equilibrate, load, and wash the packed column. In this manner the column is automatically "charged."

Once charged, the packed column may be eluted by moving the column to the elution fluid source and intaking elution fluid into the column. In this manner the column is "eluted." The column may then be moved to the elution fluid storage and the elution fluid discharged into the elution liquid storage. In this manner the elution fluid is recovered in a separate location from the other discharged fluids. The operation may then be repeated using a new column.

DESCRIPTION OF PREFERRED EMBODIMENTS

Figure 1:
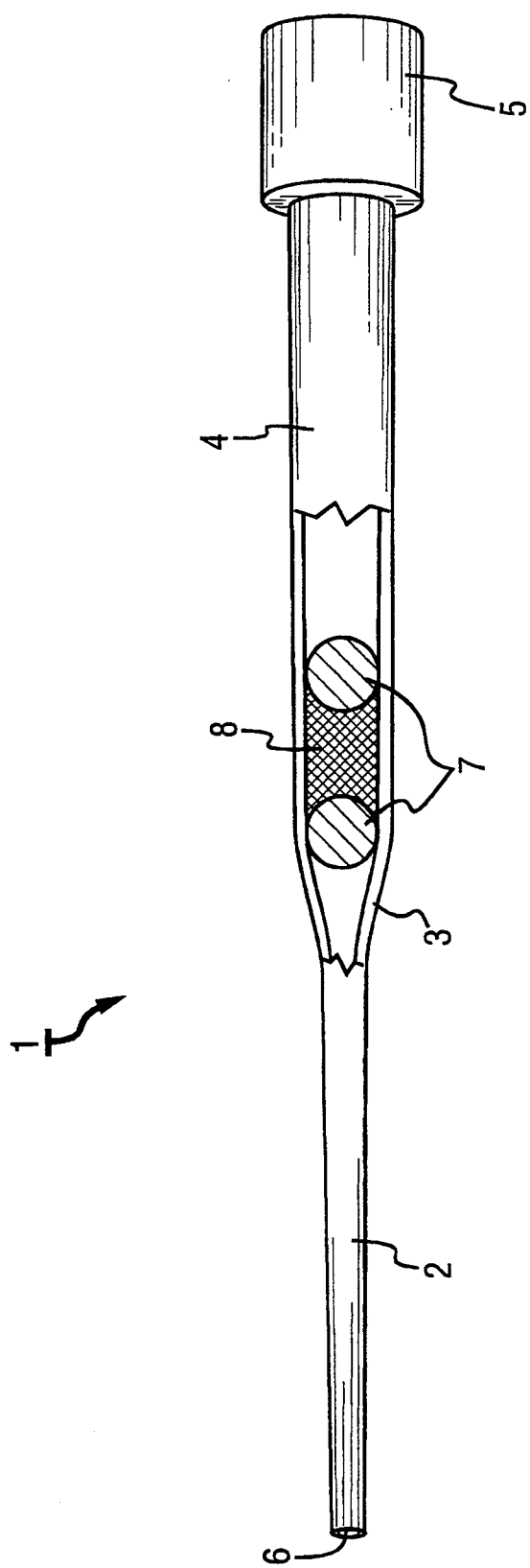
FIGURE 1 is a schematic view of a pipette tip column loaded with a chromatographic medium and porous permeable polyethylene spheres.

A Biomek® 1000 Automated Workstation (Beckman; Fullerton, Calif.) was used to implement the automatic pipetting system of this invention because it comprises a programmable robotic arm connected to a pipette tool. The pipette "tool" is the section of the Biomek® 1000 apparatus that is connectable to the pipette tip. The arm and tool are capable of vertical and horizontal (forward and backward) movement. The Biomek® 1000 is programmable and capable, among other things, of automatically moving a pipette from one location to a second location, intaking fluids into the pipette, moving the pipette to a third location, and then discharging fluid from the pipette. The pipette tool is specially designed to connect to pipette tips.

The Biomek® 1000 includes a male pipette tool which is connectable in a relatively airtight manner to the female large end of a Biomek® 1000 pipette tip. The Biomek® 1000 pipette tool intakes fluids into a pipette tip by connecting itself to the pipette tip and exerting a vacuum force on the large end of the pipette tip, thereby sucking fluids through the small end of the pipette tip and into the pipette tip. The Biomek® 1000 can be programmed to intake specific amounts of fluid into a pipette tip. Fluids are discharged from a pipette tip when the tool relaxes the vacuum force. If desired, however, the tool can be programmed to provide positive discharge air pressure to force fluid from a pipette tip.

The Biomek® 1000 may be connected to a computer to control the apparatus. In the preferred embodiments, an IBM PS/2 computer, and a commercial liquid handling program (Genesis Software Version 2.0; by Beckman) were used to control the apparatus.

In implementing the invention, radiolabeled DNA was used and binding was monitored by a liquid scintillation counter. Binding efficiencies were compared by counting the DNA solution before and after loading, counting the columns after binding, and counting the eluent. The DNA was obtained from/prepared by polymerase chain reaction using terminally labeled oligonucleotides. The liquid scintillation counter used was a Searly Analytical Inc. ISOCAP/300 6872. Appropriate liquid reagents were used for column equilibration, column loading, column washing, and column elution according to manufacturers recommendations. "Appropriate" in this context means those reagents that would adequately equilibrate, load, wash, or elute the column as desired by the practitioner. Depending on the materials examined, these reagents will vary as is well known in the art. In the particular experiments conducted herein, the equilibrating, loading, and washing fluid was 0.2M NaCl in TE (10 mM Tris-HCl, pH 7.2, 1 mM EDTA) as per the NACS PREPAC Instruction Manual, p. 12 (Bethesda Research Laboratories Life Technologies, Inc.). The eluting fluid was 2.0M NaCl in TE as described in the same NACS PREPAC Instruction Manual.

Tubular Biomek® 1000 (250 milliliter ("ml")) pipettes (Beckman catalog No. 373685) were packed to form columns for the automatic pipetting apparatus. "Packed" in the context of the invention means inserted in the pipette tip in such a manner as to resist dislodging when other materials are intaken or discharged through the pipette tip and the permeable porous material. "Binding materials" means any chemical or other chromatographic medium that will react, absorb, adsorb, or interact in some desired fashion with other materials that may flow through the pipette.

FIGURE 1 shows a packed Biomek® 1000 pipette (column) 1 which comprises a large end 5, a middle section 4 connected to the large end 5, a neck section 3 connected to the middle section 4, a tube body section 2 connected to the neck section 3, and a small end 6 connected to the tube body section 2. The Biomek® 1000 column is packed with two porous polyethylene spheres 7 and binding material 8. Binding materials 8 actually used included NACS-52 (BRL, Gaithersburg, Md.) and C18 resin (Waters, Division of Millipore, Milford, Mass.). It will be recognized that many other binding materials may be used such as well known in the art. If the liquid flowrates are critical, it may be possible to vary the bead or granule size of the binding material to allow the liquid to flow more easily through the binding material. "Porous" in the context of this application means relatively permeable to liquids but relatively impermeable to solids.

The spheres 7 may also be made of many suitable porous materials such as polyethylene. It is understood that the spheres 7 are preferably made of a soft material that will mold itself to the inside of a pipette and provide a snug fit therein. It is also understood that the word "sphere" as used in the context of this application only means objects that are roughly spherical. Irregularly shaped porous materials that will mold themselves to the shape of the interior of the pipette and provide a snug fit therein are included within this definition.

Glass wool may also be used in place of the polyethylene spheres 7, however polyethylene spheres are preferred. When glass wool was packed in a column and then topped with binding material 8, the glass wool and/or binding material 8 tended to dislodge during the intake or discharge operations of the pipetting apparatus, thus interfering with the binding or chromatographic process. When glass wool was packed both above and below the binding material 8 in the pipette 1, the pipette tool experienced difficulty in suctioning fluid into the pipette 1, and thus binding efficiency was decreased.

Porous polyethylene sheets were also cut to fit in various locations within the pipette 1 in place of the polyethylene spheres 7, however results were similar to those achieved with the glass wool. Binding efficiencies with the polyethylene sheets varied because of the non-uniformity of the packing as well as the channeling effect of improperly packed columns.

The position of the porous polyethylene spheres 7 with respect to the small end 6 of the column 1 was altered and the amount of binding material 8 was varied in different experiments. It was discovered that a preferred location of the polyethylene spheres 7 and binding material 8 was obtained by placing the polyethylene sphere closest to the small end 6 in the middle section 4 and adjacent to the neck 3.

The packing of the pipettes 1 with porous polyethylene spheres 7 required only simple tools such as forceps, a steel rod, and a scoop of known dimension. The forceps was used to place the polyethylene sphere 7 in the pipette 1. Because the pipette 1 is wedge-shaped, the sphere 7 would not pass beyond a certain point with gravity force alone. A steel rod was used to push the sphere 7 to the middle section 4 adjacent to the neck section 3. A scoop was used to add the binding material 8 on top of the sphere 7, and a second sphere 7 was then placed on top of the binding material 8. The porous polyethylene spheres 7 were commercially available 5/32 inch NEN balls from DuPont NEN Products (Boston, Mass.).

It is possible to prepare a column without using the second polyethylene sphere 7. When columns prepared in this manner were used, the Biomek ® 1000 occasionally suctioned up liquid and binding material into the pipette tool. In such situations, binding of the DNA to the binding material was relatively efficient, however the results using these columns were not highly reproducible.

The most preferred column was obtained by packing the binding material between two 5/32 inch porous polyethylene spheres 7. Using these columns, the Biomek ® 1000 was able to intake the fluids and the binding results were efficient and reproducible. These columns were packed snugly enough so that intake and discharge forces of the Biomek ® 1000 did not loosen the column. It was noted that some 96 tips could be manually packed in about 20 minutes. This packing procedure proved to be useful not only for packing columns to be used with the Biomek ® 1000, but also for cutting the expense involved in generating any number of disposable columns.

The Biomek ® 1000 has limited available space in its fluid reservoirs, and hence it was necessary to modify these reservoirs to prepare a charging fluid discard location that would not overflow. To modify the reservoir, a vacuum suction apparatus was attached to one of the Biomek ® 1000 reservoirs to allow fluids that are discarded there to be removed quickly. To attach the vacuum suction apparatus, a hole was drilled in the center of either the 37 ml (Beckman catalog No. 373690) reservoir or the 17 ml (Beckman catalog No. 373691) reservoir, a pipette tip was pushed inside, and flexible tubing was attached from the vacuum suction apparatus to the pipette tip.

The Biomek ® 1000 was programmed in a specific embodiment to use the pipette tool to perform the following steps:

(1) move to a packed column in a column storage area and connect to the column so as to allow the pipetting apparatus to intake and discharge fluid through the packed column;

(2) move the column to a equilibration fluid source reservoir and intake a specified amount of equilibration fluid;

(3) move the column to the fluid discard location and discharge the equilibration fluid at the location;

(4) move the column to the loading fluid source reservoir and intake a specified amount of loading fluid;

(5) move the column to the fluid discard location and discharge the loading fluid at the location;

(6) move the column to a washing fluid source reservoir and intake a specified amount of washing fluid;

(7) move the column to a fluid discard location and discharge the washing fluid at the location;

(8) move the column to the elution fluid source reservoir and intake a specified amount of elution fluid; and (9) move the column to elution fluid storage reservoir and discharge the elution fluid into the elution fluid storage reservoir.

The "fluid discard location" may be one location, or it may be several different locations.

Preferred results were achieved when the fluid intake processes were repeated at least once with each fluid prior to continuing on with the next step of the procedure. For instance, during the elution fluid intake process, the column was moved to the elution fluid source, the elution fluid was intaken and discharged (with the discharged elution fluid being returned immediately to the elution fluid source), and then the elution fluid was again intaken prior to moving the column to the elution storage reservoir. Similarly, the loading fluid intake process may be repeated in like manner to obtain preferred results. Alternately, the fluid intake processes may be repeated without returning the fluid immediately to the source. For instance, for the equilibration fluid intake process, steps (2) and (3), as outlined above, may be simply repeated prior to continuing on with step (5), etc.

It is anticipated that the present invention will help markedly to automate the solid phase Maxim-Gilbert sequence reactions. Moreover, other binding materials may be packed in these columns, thus automating other column applications, such as poly-A RNA preparation, avidin columns, Sephadex resin columns, and dyna beads columns.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein or the steps or the sequence of steps of the methods described herein without departing from the spirit and scope of the invention as described in the following claims.

What is claimed is:

1. An apparatus adapted to perform chromatographic analysis and capable of column equilibration, column loading, column washing, and column elution, comprising a chromatographic column with a tapered tip and which is adapted at a terminal end with a permeable plug capable of holding a charge of binding material; a source of binding material; a plurality of column chromatographic stations including at least one separate fluid dispensing station and at least one separate receptacle station; and an automatic column handler programmable to automatically engage the column in a substantially upright position so that a bottom portion of the column is proximate the tapered tip during use, move the substantially upright column sequentially between a plurality of said stations during use, receive fluid upwardly through the tapered tip into the bottom portion of the column at each dispensing station during use, and discharge fluid downwardly from the bottom portion and through the tapered tip of the column at each receptacle station during use.

2. The apparatus of claim 1 wherein the column comprises a tube containing permeable plugs configured to retain a charge of binding material between the plugs.

3. The apparatus of claim 2 wherein at least one of the plugs is removable from the column, so as to enable the column to be charged and decharged with the binding material.

4. The apparatus of claim 2 wherein the plugs are elastomeric members capable of being received within the column and held in position by internal structural features of the column.

5. The apparatus of claim 2 wherein the plugs seal against the internal wall of the column such that fluid will permeate through the body of the plug.

6. The apparatus of claim 2 wherein the plugs are spherically shaped.

7. The apparatus of claim 1 wherein the column is a pipette tip-like member having a relatively long central section with an inside diameter, and an extended necked section with an inside diameter smaller than the inside diameter of the central section.

8. The apparatus of claim 1 wherein at least one dispensing station comprises a charging fluid reservoir.

9. The apparatus of claim 8 wherein at least one charging fluid is an equilibrating fluid and the automatic column handler is programmed to equilibrate the column with the equilibrating fluid.

10. The apparatus of claim 9 wherein at least one dispensing station is an elution fluid reservoir and the automatic column handler is programmed to elute the column with elution fluid from the elution fluid reservoir.

11. The apparatus of claim 8 wherein at least one charging fluid is a loading charging fluid and the automatic column handler is programmed to load the column with the loading charging fluid.

12. The apparatus of claim 11 wherein at least one dispensing station is an elution fluid reservoir and the automatic column handler is programmed to elute the column with elution fluid from the elution fluid reservoir.

13. The apparatus of claim 8 wherein at least one charging fluid is a washing charging fluid and the automatic column handler is programmed to wash the column with the washing charging fluid.

14. The apparatus of claim 13 wherein at least one dispensing station is an elution fluid reservoir and the automatic column handler is programmed to elute the column with elution fluid from the elution fluid reservoir.

15. The apparatus of claim 1 wherein at least one dispensing station comprises an eluting fluid reservoir.

16. The apparatus of claim 1 wherein at least one dispensing station is an elution fluid reservoir and the automatic column handler is programmed to elute the column with elution fluid from the elution fluid reservoir.

17. The apparatus of claim 1 wherein at least one receptacle station comprises a charging fluid discard location.

18. The apparatus of claim 1 which further comprises a vacuum source connected to at least one receptacle station such that liquid can be removed by vacuum force from a bottom of a receptacle station during use.

19. The apparatus of claim 1 wherein at least one receptacle station comprises an elution fluid storage location.

20. An apparatus adapted to perform chromatographic analysis, comprising:
a chromatographic column with a tapered tip which is adapted at a terminal end with a permeable plug capable of holding a charge of binding material;
a source of binding material;
a plurality of column stations including at least one loading fluid dispensing station, at least one charging fluid dispensing station, at least one equilibrating fluid dispensing station, at least one eluting fluid dispensing station, and at least one receptacle station; and
an automatic column handler programmable to automatically engage the column in a substantially upright position so that the column has a bottom portion proximate the tapered tip, move the substantially upright column sequentially between a plurality of the dispensing and receptacle stations to load, charge, equilibrate, and elute the column during use such that fluid is received upwardly through the tapered tip into the bottom portion of the column at each dispensing station during use, and such that fluid is discharged downwardly from the bottom portion and through the tapered tip of the column at each receptacle station during use.

21. The apparatus of claim 20 wherein the chromatographic column comprises a permeable plug positioned at each end of the binding material.

22. The apparatus of claim 21 wherein the permeable plugs are substantially spherical in shape.

* * * * *

UNITED STATES PATENT AND TRADEMARK OFFICE
CERTIFICATE OF CORRECTION

PATENT NO. : 5,395,521
DATED : March 7, 1995
INVENTOR(S) : Pudur Jagadeeswaran

It is certified that error appears in the above-identified patent and that said Letters Patent is hereby corrected as shown below:

Column 1,
Line 6, following "BACKGROUND OF THE INVENTION", add the following paragraph:
-- The government owns rights in the present invention pursuant to grant number HL36226 from the National Institutes of Health. --.

Signed and Sealed this

First Day of November, 2005

JON W. DUDAS
*Director of the United States Patent and Trademark Office*